(12) United States Patent
Bavykin et al.

(10) Patent No.: US 7,208,269 B2
(45) Date of Patent: *Apr. 24, 2007

(54) METHOD FOR LABELING DNA AND RNA

(75) Inventors: Sergei Bavykin, Darien, IL (US); Andrei D. Mirzabekov, Moscow (RU)

(73) Assignee: U Chicago Argonne LLC, Chicago, IL (US)

( * ) Notice: Subject to any disclaimer, the term of this patent is extended or adjusted under 35 U.S.C. 154(b) by 527 days.

This patent is subject to a terminal disclaimer.

(21) Appl. No.: 10/057,753

(22) Filed: Jan. 23, 2002

(65) Prior Publication Data

US 2002/0165388 A1    Nov. 7, 2002
US 2006/0178508 A9    Aug. 10, 2006

Related U.S. Application Data

(63) Continuation of application No. 09/751,654, filed on Dec. 29, 2000, now Pat. No. 6,818,398.

(60) Provisional application No. 60/263,840, filed on Jan. 23, 2001.

(51) Int. Cl.
*C12Q 1/68* (2006.01)

(52) U.S. Cl. .......................................................... 435/6

(58) Field of Classification Search .................... 435/6, 435/91.1, 91.2, 7.7, 7.9; 436/56; 536/23.1, 536/24.3, 25.32

See application file for complete search history.

(56) References Cited

U.S. PATENT DOCUMENTS

| 4,617,261 A * | 10/1986 | Sheldon et al. ................. 435/6 |
| 5,981,734 A * | 11/1999 | Mirzabekov et al. ...... 536/25.3 |
| 6,818,398 B2* | 11/2004 | Bavykin et al. ................ 435/6 |
| 2003/0096229 A1* | 5/2003 | Bavykin et al. ................ 435/6 |

FOREIGN PATENT DOCUMENTS

WO    WO 9922020 A2 *    5/1999

OTHER PUBLICATIONS

Rosenthal et al., "Automated sequencing of fluorescently labelled DNA by chemical degradation," DNA Sequence, 1990, vol. 1 No. 1, pp. 63-71.*

* cited by examiner

*Primary Examiner*—Young J. Kim
(74) *Attorney, Agent, or Firm*—Cherskov & Flaynik

(57) ABSTRACT

A method for fragmenting and labeling nucleic acids is provided. The method comprises maintaining double- and single-stranded nucleic acid molecules in an aerobic or an anaerobic atmosphere, contacting the molecules with hydrogen peroxide and radical generating coordination complexes for a time and at concentrations sufficient to produce aldehyde moieties on the molecules, reacting the aldehyde moieties with amine to produce a condensation product, and labeling the condensation product.

15 Claims, 7 Drawing Sheets

METHOD FOR LABELING DNA AND RNA

This application claims the benefit of Provisional Application No. 60/263,840 filed Jan. 23, 2001.

This patent application is a contination application of U.S. application Ser. No. 09/751,654, filed Dec. 29, 2000, which has since issued as U.S. Pat. No. 6,818,398 B2 on Nov. 16, 2004.

CONTRACTUAL ORIGIN OF THE INVENTION

The United States Government has rights in this invention pursuant to Contract Number W-31-109-ENG-38 between the United States Government and Argonne National Laboratory.

BACKGROUND OF THE INVENTION

1. Field of the Invention

This invention relates to a method for labeling DNA and RNA, and more specifically, this invention relates to a method for labeling DNA and RNA using radical-producing chemical agents.

2. Background of the Invention

DNA microchip technology is a rapid, high throughput platform for nucleic acid hybridization reactions. However, nucleic acid fragmentation and labeling are two of the limiting steps in the development of rapid protocols for DNA microchip technology.

PCR and other amplification techniques are utilized for bacteria identification. Immunological methods and mass-spectrometry also have been adapted for this purpose, but are expensive and cumbersome.

Several enzymatic and chemical protocols are available for fluorescent labeling of nucleic acids. All of these methods are expensive and time consuming. Most of these protocols demand careful prerequisite nucleic acid isolation, fractionation (generally requiring one or more hours), labeling, separate sample fragmentation procedures and a final purification step.

Typical nucleic acid labeling methods adopt a myriad of approaches. For example, M. D. Schena et al., *Science* 270, 467–470 (1995); J. L. DeRisi et al., *Science* 278, 680–686 (1997); G. P. Yang et al., *Nucl. Acid Res.* 27, 1517–1523 (1999); K. Wang et al., *Gene* 229, 101–108 (1999), and M. Wilson et al. *Proc. Natl. Acad. Sci USA* 96, 12833–12838 all rely on effecting labeling using reverse transcriptase. Typically, this process requires from one to two hours to complete.

D. Guiliano et al. *BioTechniques* 27 146–152 (1999) and G. T. Hermanson, *Bioconjugate Techniques* (Academic Press, Inc. San Diego, Calif., 1996) utilize random priming. However, these protocols require from 3 to 10 hours to complete.

Terminal transferase protocols are featured in K. L. Gunderson et al. *Genome Res.* 8, 1142–1153 (1998) and L. Wodicka et al. *Nat. Biotechnol.* 15, 1359–1367. However, these processes also require between 1 and 2 hours to run.

Polymerase Chain Reaction (PCR) protocols for labeling are widespread. Typical references for PCR processes include R. J. Sapolsky et al. *Genomics* 33, 445 –456 (1996); M. T. Cronin et al. *Hum. Mutat.* 7, 244–255 (1996); S. Tyagi et al. *Nat. Biotechnol* 16, 49–53 (1998); and P. N. Gilles et al. *Nat. Biotechnol* 17, 365–370 (1999). However, PCR protocols require between 1 and 2 hours to complete.

A need exists in the art for a simple protocol for labeling nucleic acids found either in DNA or RNA. The protocol should require mild conditions of reaction and should yield high amounts of cross-linked complexes in short incubation times. The method should facilitate both the labeling and fragmentation at random sites of nucleic acids, therefore being independent of sequence or two dimensional structures. The method should facilitate the end-labeling of nucleic acids and further accommodate a broad number of label derivatives, the later to be attached to nucleic acids. Lastly, the method should accommodate automated processes.

SUMMARY OF THE INVENTION

It is an object of the present invention to provide a method for labeling nucleotide molecules that overcomes many of the disadvantages of the prior art.

Another object of the present invention is an economical method for labeling DNA and RNA molecules. A feature of the invention is that a product of the labeling method is a Schiff base comprising the nucleic acid and the label. An advantage of the method is that the method is independent of nucleic acid sequences of the probe. Another advantage is that the method facilitates manipulation of both DNA and RNA.

Yet another object of the present invention is to provide a method for modifying nucleic acid. A feature of the invention is that the modification occurs aerobically and anaerobically in the presence of hydrogen peroxide to ultimately lead to the formation of a Schiff base for subsequent labeling. An advantage of the present method is that the Schiff base is reduced and labeled simultaneously to provide a streamlined nucleic acid and labeling protocol.

Briefly, the invention provides a method for labeling nucleic acids, the method comprising maintaining double-stranded nucleic acid molecules in an aerobic and anaerobic atmosphere; contacting the molecules with hydrogen peroxide and nuclease for a time and at concentrations sufficient to produce aldehyde moieties on the molecules; reacting the aldehyde moieties with amino derivatives of fluorophores, or with any other label containing primary amino groups, or with an amine to produce a condensation product; and labeling the condensation product.

BRIEF DESCRIPTION OF THE DRAWING

The present invention together with the above and other objects and advantages may best be understood from the following detailed description of the embodiment of the invention illustrated in the drawing, wherein.

DETAILED DESCRIPTION OF THE INVENTION

Figure 1:
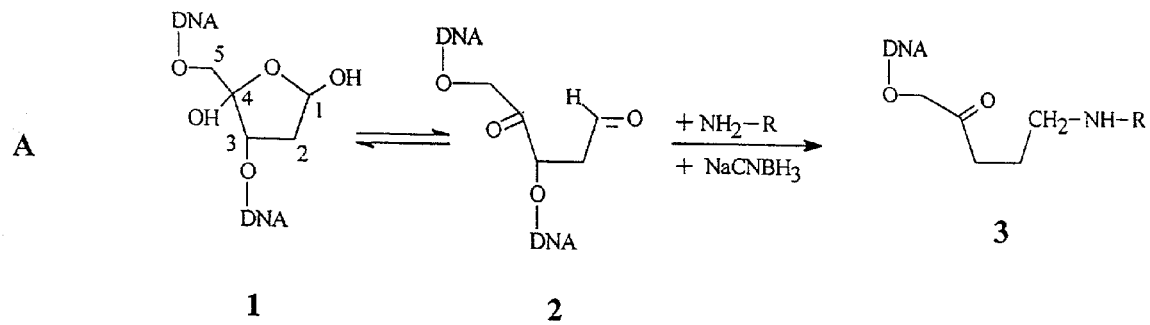
FIG. 1 is a reaction sequence of DNA labeling, in accordance with features of the present invention.
Figure 1:
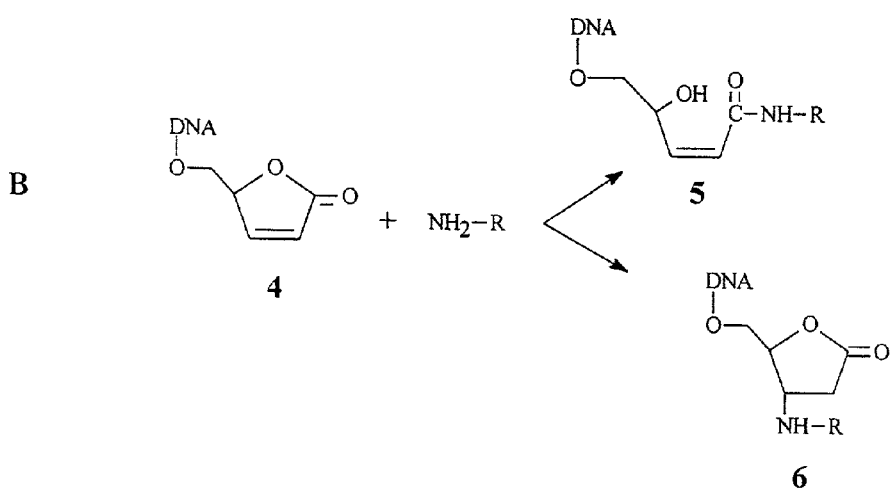
Figure 1:
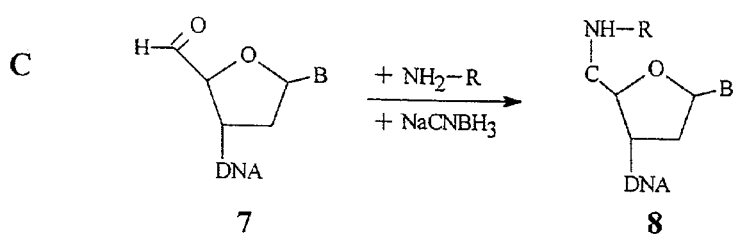

A method for simultaneous sequence non-specific end-labeling and fragmentation of double-stranded and single-stranded nucleic acids is presented herein. The method uses redox-reactive coordination complexes to fragment and label RNA and DNA. These labeled nucleic acids were found highly effective for hybridization with DNA microchips containing oligonucleotide probes. The invented protocols which have been developed for the fragmentation and labeling of RNA and DNA may also be used for the fragmentation and labeling of DNA prior to microchip hybridization. The invented protocols utilize radical generating moieties to provide two reactions simultaneously, labeling and fragmentation, for both RNA and DNA.

In the labeling reactions, fluorescent dye is incorporated mostly to 3' and 5' ends of nucleic acid fragments. This end labeling feature without excessive concomitant nucleobase modifications renders fragments for use in recognizing and differentiating short sequences containing a few mismatches. Generally, the protocols are run at temperatures ranging from 30 C. to 95 C. Operating the protocols at temperatures approaching the boiling point of water, or in the presence of a denaturing agent (such as urea formamide, or guanidine chloride), confers unfolding of the nucleic acids. This unfolding facilitates the production of high yields of labeling and fragmentation, while eliminating the influence of two-dimensional (2-D) structure on the protocol. This protocol is particularly advantageous when working with RNA inasmuch as RNA often has complicated 2-D structure.

Specifically, the inventors have utilized oxidants, which have free radical characteristics, to facilitate the labeling of nucleic acids. The advantages of the radical-mediated labeling methods are simplicity and high speed. In addition, the reactions are run at any temperature selected below the boiling point of water, and preferably from between 30° C. and 95° C.

The chemical radical-producing agents serve as chemical nucleases in the invented method to produce single-stranded breaks in nucleic acid probes. A myriad of coordination complexes are utilized in the invented method, including, but not limited to, 1,10-phenanthroline-Cu(II) (hereinafter referred to as OP-Cu), bleomycin-Fe(III) (hereinafter referred to as BLM-Fe), EDTA-Fe, ascorbic acid-Cu, methylene-blue-Cu, metallogporphyrins, and other chemical nucleases.

These radical producing complexes generate amine-hydrazide-nucleic acid crosslinking under anaerobic conditions. For example, in the presence of hydrogen peroxide under anaerobic conditions, the BLM-Fe complex catalyzes the formation of free nucleic acid bases and the aldehyde form of deoxyribose at the abasic site of the DNA backbone. The backbone typically undergoes scission in the presence of alkali or amines.

Generally, the invention embodies a two step method for labeling DNA and RNA molecules with compounds containing primary amines. First, DNA or RNA is modified under anaerobic conditions with hydrogen peroxide, a coordination complex, and chemical nucleases. Under anaerobic conditions, hydrogen peroxide and the nucleases produce free radicals which attack the nucleic acids, resulting in the formation of free nucleic acid bases and the aldehyde forms of ribose or deoxyribose (See Equation 1).

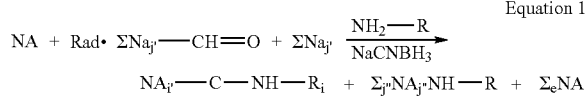

Equation 1 wherein NA designates nucleic acid and Rad. is the product of a chemical radical production, of the type discussed supra. $NH_2$—R represents a compound having at least one primary amino group and a second group which facilitates the attachment of a label (e.g. ethyl diamine) in an indirect labeling protocol. Alternatively $NH_2$—R represents a compound comprising a fluorescent dye conjugated with primer containing a primary amine in a direct labeling protocol. As such, exemplary $NH_2$—R candidates include, but are not limited to an amino-derivative of fluorophores, or any label containing a primary amino group. $NaCNBH_3$ is a reducing agent, $\Sigma Na_{j'}$—CH=O depicts an intermediate nucleic-acid form containing the aldehyde or ketone moiety, typically on the 5' carbon or on the sugar (ribose) itself. $\Sigma Na_{j}$, represents all other nucleic acids not containing the aldehyde or ketone moiety. $\Sigma_{j''} NA_{j''} NH$—R represents moieties resulting from the attachment of a primary amine compound to nucleic acid moieties not containing aldehyde groups, and $\Sigma_e NA$ represents other modifications of the starter nucleic acid pool, but which are not involved in the cross linking reaction, The reactive aldehyde- or ketone-group on the DNA and RNA thus serves in the second step of the method as the substrate for subsequent labeling reactions.

In the second step of the method, a primary amine is combined with the aldehyde- or ketone-group in a condensation reaction to produce a Schiff base or amides. The Schiff base is reduced and the product of this reduction step is labeled with a desirable tag. Alternatively, and as depicted above in Equation 1, the reduction and labeling step can be combined. The reduction and/or labeling processes can be done in aerobic or anaerobic conditions.

The invented method produces high yields of crosslinked complexes. The method is effective independent of the nucleic acid sequence or the two-dimensional structure of nucleic acids. The same invented protocol can be utilized to label both DNA and RNA. The resulting labeled products are effective probes in hybridization experiments.

Reaction Chemistry Detail

Figure 2:
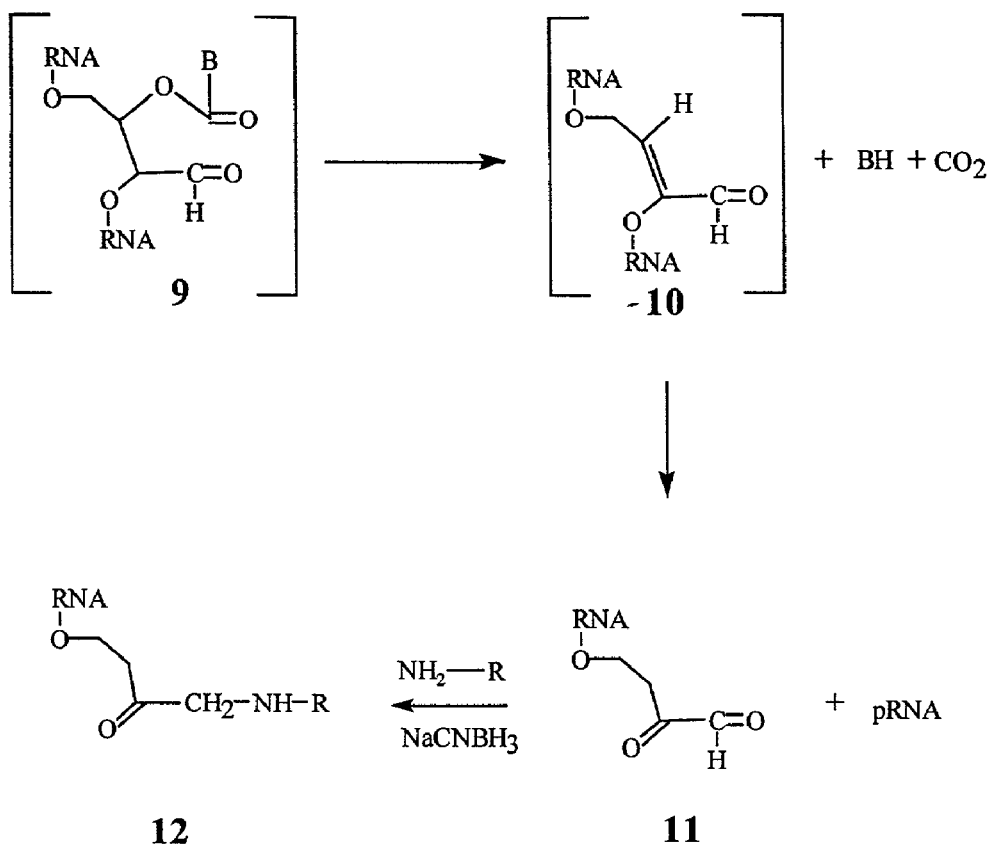
FIG. 2 is a reaction sequence of RNA labeling, in accordance with features of the present invention.

FIGS. 1 and 2 depict the mechanisms for dye cross linking to modified DNA and RNA, respectively. Hemiacetal, lactone, and 5'aldehyde are the common intermediates in the oxidative strand scission of nucleic acids by radical-generating agents. These intermediates appear after base elimination has occurred and they may serve as cross-linking sites for primary amines in the invented radical-mediated nucleic acid labeling procedure.

The H-5'abstraction pathway under both aerobic and anaerobic conditions often results in the production of an oligonucleotide 5'-aldehyde (FIG. 1C). The aldehyde interacts with amines through the formation of a Schiff base in the same manner as described for the H-4' anaerobic pathway. (FIG. 1A). For this labeling reaction, the presence of sodium cyanoborohydride in the reaction buffer or immediate sodium cyanoborohydride treatment following Fe-EDTA treatment is desirable for fast Schiff base reduction and production of a stable covalent complex, such as Molecule number 8 of FIG. 1.

Radicals generated with such redox-active coordination complexes as OP-Cu and Fe-EDTA effectively attack both DNA and RNA. The treatment of identical RNA and DNA sequences with OP-Cu complexes linked to carrier oligonucleotides shows that both the cutting sites and the kinetics of fragmentation are similar for RNA and DNA. In addition, OP-Cu effectively cross-links histones both to riboligonucleotides and to deoxyribooligonucleotides as well as to DNA in bulk chromatin in vitro and in vivo. OP intercalates into the minor grove of B-form DNA and as such OP-Cu cleaves dsDNA more readily then ssDNA. Generally, for RNA, OP-Cu degrades loop regions more quickly than duplex regions.

Another possible difference in the reaction of OP-Cu with DNA and RNA is that the punitive intermediate as depicted in FIG. 2, (Molecule No. 9) suggested for the RNA H-1' abstraction pathway is a candidate for crosslinking with primary amines, resulting in the formation of stable products.

The inventors have found that radical mediated labeling seems to be an effective method for placing the majority of the dye on the ends of the nucleic acid fragments. Radical mediated labeling results in the crosslinking of the fluorescent dye to the 5'- or 3'-end of the nucleic acid strand. In addition, the inventors found that in OP-Cu-mediated protein-DNA crosslinking, the crosslinking occurs at the 5'-end or the 3'-end of the DNA molecule in approximately 90% of the cross-linked complexes, and crosslinking occurs randomly along the DNA fragment in approximately 10% of the complexes.

In this detailed description, the radical-producing complexes OP-Cu and Fe-EDTA are featured for illustrative purposes only. As such, other radical producing complexes compatible with preselected labels and target nucleic acids also are suitable.

The inventors have determined that redox-active coordination complexes such as OP-Cu and Fe-EDTA can be effectively used for sequence-dependent nucleic acid fragmentation and labeling with fluorescent dyes as part of a DNA microchip protocol. Radicals generated with OP-Cu and Fe-EDTA effectively attack both DNA and RNA. RNA treated with the OP-Cu and the Fe-EDTA protocols was highly suitable for hybridization with DNA microchips containing oligonucleotide probes specific for the Bacillus group of microorganisms. The inventors also demonstrated that both the OP-Cu and the Fe-EDTA protocols were effective for the fragmentation and labeling of DNA. Generally, OP-Cu and FeEDTA serve as radical-generating chemical complexes.

As depicted in FIG. 1, A, five carbon atoms of the DNA sugar residue have a total of seven hydrogen atoms available for abstraction by an oxidizing agent. The main pathway of DNA cleavage by OP-Cu is H-1 abstraction. OP-Cu also cleaves DNA with H-4 abstraction. OP-Cu degradation is associated with some slight sequence specificity.

The Fe-EDTA complex is negatively charged and so does not interact directly with the DNA molecule. Instead, the Fe-EDTA complex, in the presence of hydrogen peroxide, produces hydroxyl radicals (OH.) which have no charge and are therefore able to diffuse into the molecule. Abstraction of the H-4 and H-5 are the predominant pathways. Preference for individual hydrogen atoms was H-5>H-4>H-2=H-3>H-1.

H-4 abstraction under anaerobic conditions results in nucleobase release with the production of a hemiacetal intermediate (FIGS. 1A, 1) that is in equilibrium with the aldehyde form of deoxyribose (FIG. 1A, 2). Anaerobic conditions were utilized to optimize amine cross-linking. Generally, oxygen was reduced in reactants and reactant solutions by bubbling with argon. The inventors found that, at least for Op-Cu oxidation protocols, a 15 percent increase in hybridization signal was realized when anaerobic conditions were utilized.

The aldehyde group generated by the initial oxidation step is attacked by a nucleophilic moiety (such as a primary amine or a hydrazide), creating a reversible covalent bond (Schiff base). The resultant imine undergoes spontaneous conversion with the 3'phosphodiester bond cleaved by the mechanism of β-elimination. This facilitates the simultaneous cross-linking of amine or hydrazine derivatives of the fluorescent dyes to the modified DNA at the same time as fragmentation occurs.

Figure 3:
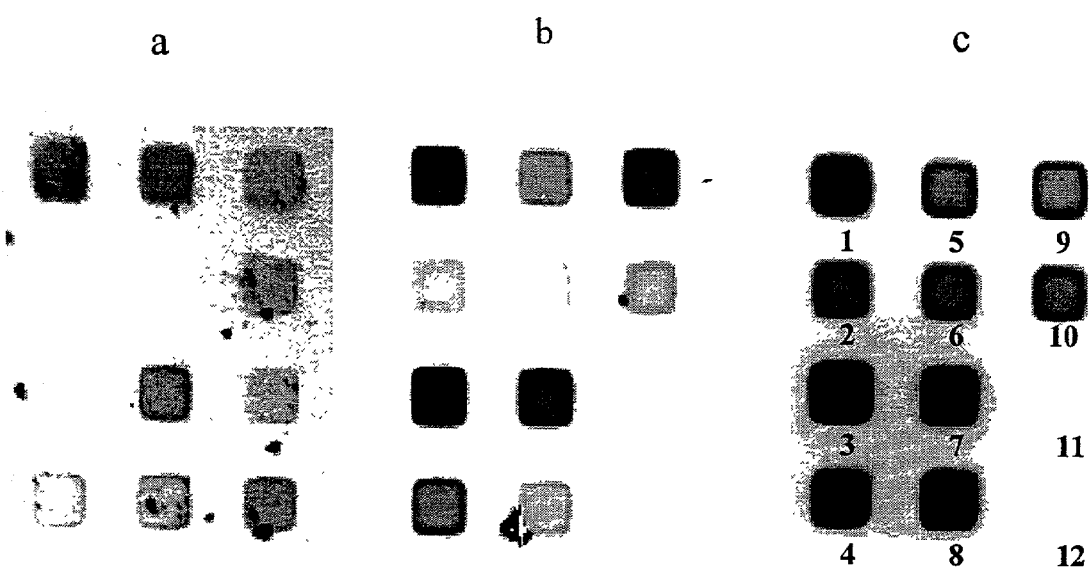
FIG. 3 is an illustration of fragmentation and hybridization of *B. thuringiensis,* using the invented protocol in accordance with features of the present invention.

After fragmentation and cross-linking, reduction of the Schiff base with sodium cyanoborohydride is desirable for production of the final labeled product, (FIGS. 1A, 3). This prevents removal of the cross-linked dye by δ-elimination.

Figure 5:
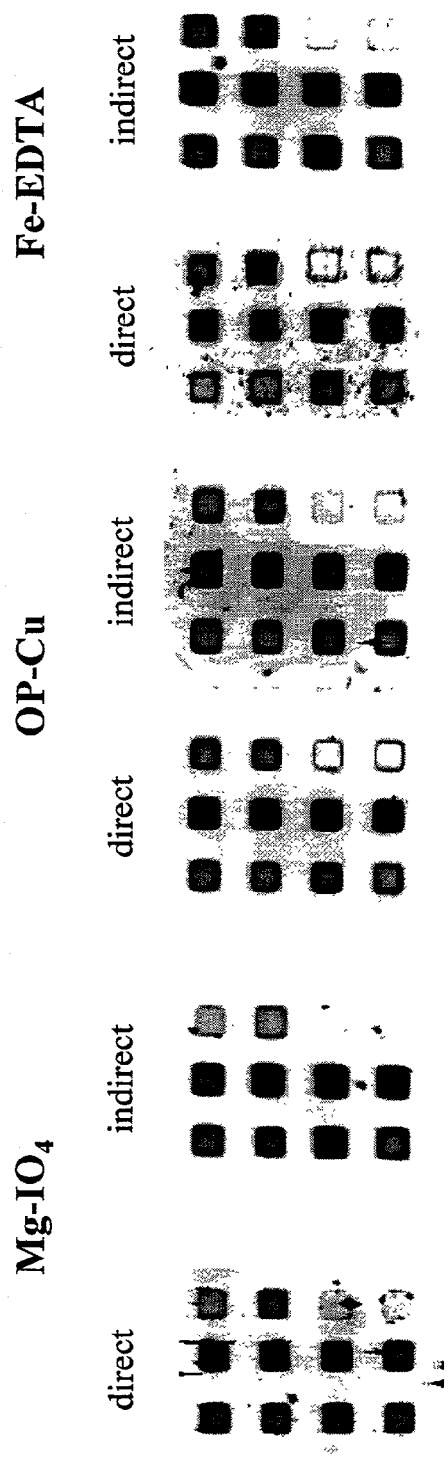
FIG. 5 is a comparison for different fragmentation protocols, in accordance with features of the present invention.
Figure 6:
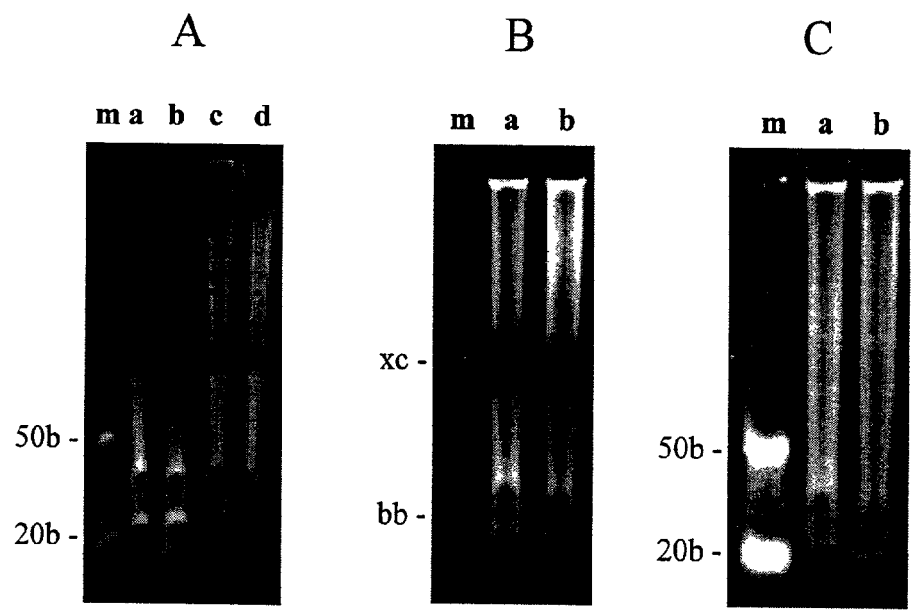
FIGS. 6A–C illustrate the effect of reducing agent on fragmented and labeled nucleic acids, in accordance with features of the present invention.

Another DNA intermediate used for labeling with amino-derivatives of fluorescent dyes is meta-stable lactone in FIG. 1B. Reaction of this lactone with a primary amine leads to two labeled products, (FIGS. 1B, 5, 6).

The H-5' abstraction pathway under both aerobic and anaerobic conditions results in the production of an oligonucleotide 5'-aldehyde, as depicted in FIG. 1, C. In one scenario, the aldehyde reacts with amines through the formation of a Schiff base in the same manner as described for the anaerobic pathway depicted in FIG. 1A. In this labeling reaction, the presence of sodium cyanoboro-hydride in the reaction buffer or immediate sodium cyanoborohydride treatment following Fe-EDTA treatment is desirable for fast Schiff base reduction and subsequent production of a stable covalent complex 8.

Figure 4:
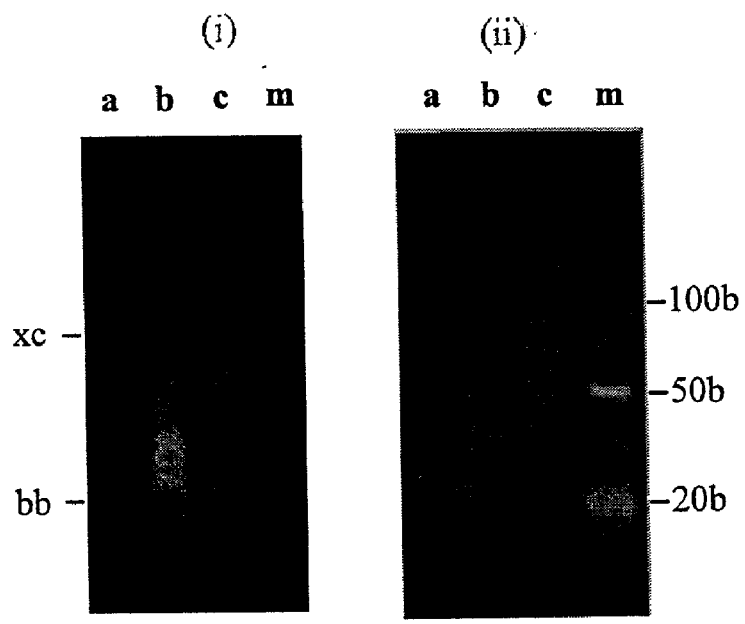
FIGS. 4A–B are illustrations of the electrophoresis of labeled/fragmented nucleic acids under denaturing conditions, with (i) showing fluorescence under direct light and (ii) showing ethidium bromide stained gel.
Figure 4:
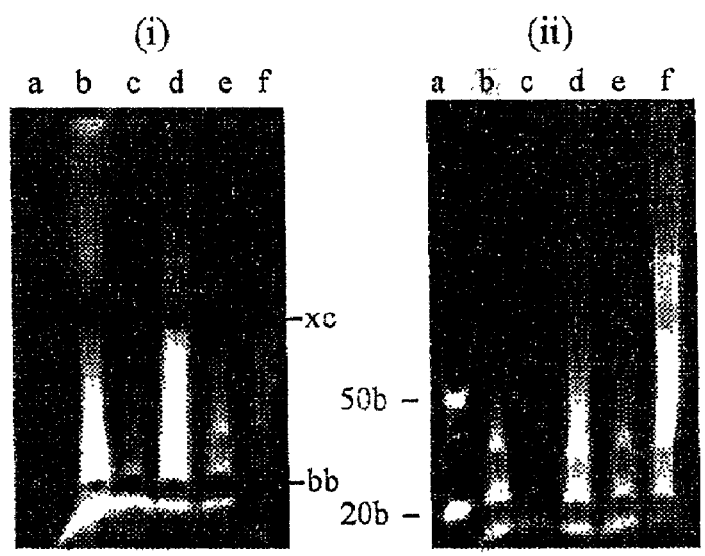

FIG. 2 depicts differences in labeling protocol between DNA and RNA. Specifically, the presence of the hydroxyl group in the 2'-position of ribose results in the production of a putative intermediate, (FIGS. 2A, 9) instead of lactone 4 (of FIGS. 1B, 4) produced in the DNA manipulation. This lactone is able to react with primary amines to form an amide (FIGS. 2A, 10), or a Schiff base with an aldehyde group. The Schiff base then can be reduced to produce a stable complex (FIGS. 2A, 11). The putative intermediate (FIGS. 2B, 9) serves as a substrate for cross-linking with primary amines to form stable labeled products (FIGS. 2A, 12).

The inventors have found that linking the dye to the end of the nucleic acid fragment is more useful than having the dye randomly localized along the fragment. Having the dye at the end of the fragment causes minimal steric interference during subsequent hybridization. The invented method of using radical mediated labeling is an effective method for placing the majority of the dye on the ends of the nucleic acid fragments.

In summary, radical mediated labeling results in the cross-linking of the flourescent dye to the 5'- or 3'-end of the nucleic acid strand, as depicted in FIGS. 1 and 2.

Generally, two protocols, direct and indirect, have been developed to facilitate the fragmenting and labeling of nucleic acids. Both protocols can be utilized with a broad spectrum of derivatives of fluorescent dyes and at a wide range of temperatures. The high temperature of reaction, or alternatively the possibility of using a high concentration of a denaturant such as urea, make the labeling-fragmentation reaction non-dependent from the two-dimensional structures of the subject nucleic acid, while also producing a high yield of reaction.

A schematic representation of the direct protocol is as follows:

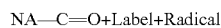

wherein NA—C=O represents a nucleic acid with an aldehyde moiety attached thereto.

A schematic representation of the indirect protocol is as follows:
 a) NA—C=O+Amine-containing Intermediate+Radical;
 b) NA—C-Amine-containing moiety+Label.

For the direct labeling protocol, the active aldehyde, lactonic, or oxicarbomide groups produced within the sugar moiety may be directly cross-linked with amine or hydrazine conjugates of fluorescent dyes. The fluorescent dye Lissamine rhodamine B ethylenediamine (LissRhod) was used for direct labeling of both RNA and DNA. The resultant Schiff base was subsequently reduced with sodium cyanoborohydride or sodium borohydride.

In the first stage of the indirect labeling protocol, a compound containing a primary amine and another reactive moiety to accommodate labels (e.g. (EDA) is cross-linked to the nucleic acids instead of the fluorescent dye, forming a Schiff base. In the next stage, the amino-modified nucleic acid may be cross-linked to fluorophores containing amino-reactive groups, such as sulfonyl chlorides, isothiocyanates, succinimidyl conjugates, fluorescamine, aromatic dialdehydes (such as OPA, NDA, or ADA) or ATTO-TAG reagents. For the indirect labeling protocol, Texas Red sulfonyl chloride (TexRed) was used for labeling both RNA and DNA. The indirect labeling protocol is especially useful for dyes that are unstable in the presence of radicals, since the labeling step occurs after the radical fragmentation reaction has been completed.

Aerobic and Anaerobic Environment Detail

The proposed mechanisms of DNA degradation via hydrogen atom abstraction can be influenced by the presence of oxygen. Most of these reactions, with the exception of H-4' abstraction under aerobic conditions, result in nucleobase release with the formation of intermediates which may react with primary amines and thus may be used for DNA crosslinking with aminoconjugates of fluorescent dyes (Scheme 1). Alternatively, these intermediates may also be cross linked with EDA and subsequently labeled with amino reactive fluorophores.

H-4'abstraction under anaerobic conditions results in nucleobase release with the production of a hemiacetal intermediate that is in equilibrium with the aldehyde form of deoxyribose (Molecule 2, FIG. 1A). The aldehyde group may be attacked by a nucleophilic moiety (such as a primary amine or a hydrazide), creating a reversible covalent bond (Schiff base), and the resultant imine undergoes spontaneous conversion in which the 3'-phosphodiester bond is cleaved by the mechanism of b-elimination. In this way, the crosslinking of amine or hydrazine derivatives of the fluorescent dyes to the modified DNA can occur at the same time as the fragmentation. After the fragmentation and crosslinking, reduction of the Schiff base with sodium cyanoborohybride is desirable for production of a stable covalent bond, thus preventing removal of the cross-linked dye by β-elimination.

In contrast to the H-4'anaerobic pathway, H-4' abstraction under aerobic conditions leads to the complete splitting of deoxyribose, and the intermediates of this pathway may not be used for labeling with aminoconjugates. Because the proposed H-4'abstraction pathways indicate that amine crosslinking might be less effective under aerobic conditions, anaerobic conditions were used in this study.

To achieve anaerobic conditions, oxygen levels in all reactants and reaction solutions can be reduced by bubbling with neutral fluid (e.g. a noble gas). The OP-Cu and Fe-EDTA direct protocols were run both with and without argon bubbling using *Bacillus cereus* bulk RNA. The results indicated that argon bubbling had little effect in the OP-Cu fragmentation process and had no impact on fragmentation for the Fe-EDTA protocols (FIG. 6B). Also, for the OP-Cu protocol, argon bubbling resulted in a 15% increase in hybridization signal. Therefore, using argon bubbling with the OP-Cu procedure will give optimal results. However, depending on the application, a 15% loss in signal may be acceptable to reduce the complexity and time of the procedure. If a small loss in signal is acceptable, then removal of the argon bubbling is an option for the OP-Cu procedures. For the Fe-EDTA protocol, the results were reversed. For Fe-EDTA, removal of argon bubbling resulted in a 14% increase in hybridization signal.

Both the OP-Cu and the Fe-EDTA protocols were ran using 16S rDNA, which was produced by PCR amplification of bulk DNA from *Bacillus cereus* 3329. The OP-Cu protocol was run in the manner described supra for both the direct and indirect protocols for RNA. Direct labeling-fragmentation reaction was performed with 15 mM OP, 1.5 mM Cu, 100 mM $H_2O_2$, 1 mM LissRhod at 45° C. for 30 min under argon bubbling and followed by reduction by 20 mM $NaCNBH_3$. Indirect reaction was carried out with 1.5 mM OP, 0.15 mM Cu, 10 mM $H_2O_2$, 50 mM EDA at 45° C. for 30 min under argon bubbling, followed by reduction by 20 mM $NaCNBH_3$, and labeled with 12.5 mM TexRed.

RNA/DNA-labeling with OP-Cu

OP-Cu binds to double stranded DNA in the minor groove, and in the presence of hydrogen peroxide, promotes DNA cleavage by the abstraction of a hydrogen atom. Five carbon atoms of the DNA sugar residue have a total of seven hydrogen atoms which are available for abstraction by an oxidizing agent. The main pathway of DNA cleavage by OP-Cu is H-1' abstraction, but OP-Cu can also cleave DNA by a minor pathway that begins with abstraction of H-4'. The degradation of DNA by OP-Cu has some slight sequence specificity.

Treatment of identical RNA and DNA sequences with OP-Cu complexes linked to carrier oligonucleotides has demonstrated that both the cutting sites and the kinetics of fragmentation are similar for RNA and DNA.

A myriad of different concentrations, temperatures and reaction times are suitable to run the protocol. Suitable concentrations of all reagents range from 0.01 mM to 1000 mM at temperatures ranging from 10° C. to 100° C. Exemplary reactant concentrations, temperatures and times are illustrated in Table 1, infra. Generally however, OP concentrations of between 1.5 and 15 mM and copper concentrations of from 0.15 and 1.5 were suitable. $H_2O_2$ concentrations of between 10 and 100 mM also provided good results. Temperatures of between 30° C. and 45° C. produced good results.

The inventors found that the Op-Cu protocol was highly effective for RNA fragmentation and labeling when run at temperatures below the boiling point of water (i.e. 100° C.), preferably between 45° C. and 100° C. and most preferably at approximately 95° C. Reaction times will vary from a few seconds to several hours depending on temperature. For example, with a reaction temperature of 95° C., a reaction time of approximately 1–2 minutes is all that is required. With reaction temperatures of approximately 45° C., a 30 minute reaction time may be required. A reaction temperature of 0° C. will require a reaction time of approximately 2 hours. In light of the foregoing, for some applications, such as field applications where energy input is a consideration, a low reaction temperature can be an advantage.

Indirect OP-Cu Protocol

A first stage in the indirect labeling protocol is a cross linking of ethylenediamine (EDA) to the nucleic acids, instead of to the fluorescent dye. This produces the condensation product, i.e., the Schiff base. Next, the amino-modified sugar is fluorescently labeled with sulfonyl chlorides, isothiocyanates, succinimidyl conjugates, fluorescamine, aromatic dialdehydes such as OPA, NDA, ADA or ATTO-TAG reagents.

Texas Red sulfonyl chloride (TexRed) was used for indirect labeling of both RNA and DNA.

The indirect labeling protocol is particularly useful for dyes that are unstable in the presence of radicals, since the labeling step occurs after the radical fragmentation reaction has been completed.

Electrophoresis of RNA indirectly labeled under denaturing conditions revealed that increasing the OP-Cu and hydrogen peroxide concentrations resulted in a decrease in RNA length. A suitable condition for indirect labeling was treatment with 1.5 mM OP/0.15 mM Cu/10 mM H2O2 and heating at 45° C. for 30 minutes. RNA fragments between 50 b and 100 b are produced with this protocol. Clearly defined hybridization signals also result.

FIG. 3 shows hybridization of a microchip with bulk *B. thuringiensis* RNA fragmented and labeled via the OP-Cu indirect labeling protocol. The label used was TexRed. The numbers in the figure indicate the probes listed in Table 1.

Screening of several different reactant concentrations demonstrated that a preferred protocol for indirect labeling with OP-Cu includes concentrations of 1.5 mM OP/0.15 mM Cu/10 mM $H_2O_2$, at 45° C. for 30 minutes. These concentrations resulted in the strongest hybridization signal (Table 3, treatment 3 and FIG. 3, c) and RNA fragments between approximately 50 and 100b in length (FIG. 4A, c). Increasing the hydrogen peroxide concentration 10 times to 100 mM resulted in a decrease in the hybridization signal (Table 3, treatment 2 and FIG. 3b) and a decrease in the RNA length (FIG. 4A, b). Increasing the concentrations of all reagents 10 times to 15 mM OP/1.5 mMCu/100 mM $H_2O_2$ resulted in almost complete degradation of the RNA (FIG. 4A, a) and a further decrease in the hybridization signal (FIG. 3a and Table 3, treatment 1).

There are some unexpected differences in the reactions of OP-Cu with DNA and RNA. For example, because OP intercalates into the minor groove of B-form DNA, OP-Cu cleaves dsDNA more efficiently then ssDNA. However, for RNA, OP-Cu degrades loop regions more quickly than duplex regions. This difference in the reactions for DNA and RNA may be due to steric effects. The protocol utilized for OP-Cu treatment is based on that disclosed for protein-nucleic acid cross-linking, in S. G. Bavykin et al. *Anal. Biochem.*, (1998) 263, 26–30, and incorporated herein by reference.

As noted supra, OP-Cu binds to double stranded DNA in the minor groove. In the presence of hydrogen peroxide, OP-Cu promotes cleavage by the abstraction of a hydrogen atom. The main pathway of DNA cleavage by OP-Cu is H-1 abstraction. OP-Cu also can cleave DNA via H-4 abstraction (See FIGS. 1A, 1).

Direct OP-Cu Protocol

In the direct labeling protocol, nucleic acid treatment of OP-Cu results in the production of active aldehyde, lactonic, or oxicarbomide groups within the sugar moiety. These groups are then directly cross-linked with amine or hydrazine conjugates of fluorescent dyes in a condensation step. The resultant Schiff base is subsequently reduced with a suitable reducing agent. Exemplary reducing agents include, but are not limited to, sodium cyanoborohydride and sodium borohydride.

In order to optimize the direct OP-Cu protocol, experiments with different concentrations of reactants were conducted with variations in temperature and time of reaction. Reaction times of between 10 and 30 minutes are appropriate. Exemplary reaction concentrations, temperatures and times are illustrated in Table 1. Results of the invented labeling method were compared with the results obtained using the Magnesium-Sodium Periodate method discussed supra. Strongest hybridization signals were obtained with 1.5 mM OP, 0.15 mM Cu, and 10 mM $H_2O_2$ at 95° C. for 30 minutes, and also when concentrations were 15 mM OP, 1.5 mM Cu, and 10 mM $H_2O_2$ at 95° C. for 10 minutes.

For the direct OP-Cu labeling procedure, screening experiments (Table 1, FIG. 5) demonstrated that the optimal reactant concentrations were 15 mM OP/1.5 mM Cu/100 mM $H_2O_2$. These concentrations produced a strong hybridization signal. FIG. 5 shows the effect of urea on direct OP-Cu and FeEDTA labeling-fragmentation of RNA.

To determine if the OP-Cu reaction could be run more quickly, experiments were conducted with variations in temperature and time of reaction (Table 5). The strongest hybridization signals were obtained with 1.5 mM OP/0.15 mM Cu/10 mM $H_2O_2$ at 95° C. for 30 min. and with 15 mM OP/1.5 mM Cu/10 mM $H_2O_2$ at 95° C. for 10 min. (Table 5, treatment 4 and 7). Thus, the OP-Cu reaction can be shortened to 10 minutes if the temperature is raised to 95° C.

A variation of the OP-Cu protocol was run in which the reductant $NaCNBH_3$ was included in the reaction step, as depicted in FIG. 1A. This contrasts to the standard protocol wherein the reduction step is carried out after the scission reaction has been completed. The inclusion of the reductant in the reactant step produced an equivalent level of both fragmentation and hybridization signal to the invented protocol. However, this combining of scission and reduction procedures reduced the time for fragmentation and labeling by 30 minutes.

An exemplary procedure to effect a direct OP-Cu protocol is as follows: To maintain anaerobic conditions, all reagents were bubbled with argon for 15 seconds before use, and the reaction solutions were bubbled with argon for 15 seconds between each step. Total reaction volume was 100 μl. RNA (10 or 20 μg), 20 μl of 100 mM sodium phosphate (pH=7), 7M urea, and DEPC treated $H_2O$ were combined and bubbled with argon. After addition of o-phenanthroline hydrochloride monohydrate (OP) (Fluka, Ronkonkoma, N.Y.), $CuSO_4 \times 5\ H_2O$ (Cu), and 1 μl of 100 mM LissRhod, solution was bubbled with argon and preheated for 3 minutes. The solution was again bubbled with argon and $H_2O_2$ was added. The reaction solution was then bubbled with argon and heated for 10 to 30 min. Reaction was stopped by addition of 2 μl 0.5M EDTA and incubation in a room temperature water bath for 1 min. Reduction was carried out by addition of sodium cyanoborohydride to 20 mM and incubation at room temperature in the dark for 30 min. RNA was precipitated in 96% ethanol/0.4M sodium acetate at −80° C. for 20 min. After centrifugation at 14,000 rpm for 5 minutes, RNA pellets were washed twice with ethanol. Excess LissRhod was removed from RNA by butanol treatment as described above and RNA pellets were suspended in 10 to 20 μl DEPC $H_2O$.

TABLE 1

Comparison of Hybridization Signals of Direct and Indirect RNA labeling via Mg2+, OP-Cu, and Fe-EDTA Methods

| Method | Reaction Conditions | | Reactant Concentrations | Hybridization Signal (u/μg/sec) |
| --- | --- | --- | --- | --- |
| | Temp (° C.) | Time (min) | | |
| $Mg^{2+}$ Direct | 95 | 40 | 60 mM $Mg^{2+}$ | 844 |
| $Mg^{2+}$ Indirect | 95 | 40 | 60 mM $Mg^{2+}$ | 1142 |
| Fe-EDTA Direct | 95 | 10 | 1.5 mM Fe-EDTA 10 M $H_2O_2$ | 870 |
| Fe-EDTA Indirect | 95 | 10 | 1.5 mM Fe-EDTA 1 mM $H_2O_2$ 1 mM $H_2O_2$ | 1094 |
| OP-Cu Direct | 45 | 30 | 15 mM OP 1.5 mM Cu 100 mM $H_2O_2$ | 949 |

TABLE 1-continued

Comparison of Hybridization Signals of Direct and Indirect RNA labeling via Mg2+, OP-Cu, and Fe-EDTA Methods

| Method | Reaction Conditions | | | Hybridization |
|---|---|---|---|---|
| | Temp (° C.) | Time (min) | Reactant Concentrations | Signal (u/µg/sec) |
| OP-Cu Indirect | 45 | 30 | 1.5 mM OP 0.15 mM Cu 10 mM $H_2O_2$ | 1309 |

The fluorescent dye Lissamine rhodamine B ethylenediamine (LissRhod) was utilized in the direct labeling of both RNA and DNA.

For direct labeling of RNA, 10 times higher OP-Cu concentrations than that used in the indirect protocol produced the same average RNA lengths as produced by the indirect method. This difference was probably due to the lesser amounts of amine utilized in the direct protocol versus the indirect labeling protocol.

The optimal direct and indirect OP-Cu protocols resulted in identical hybridization patterns (FIG. 5) and both produced strong hybridization signals. Optimal reactant concentrations for the direct labeling protocol are 10 times higher than the optimal concentrations for the indirect labeling protocol.

The quantum yield of TexRed conjugates has been found to be higher than the quantum yield of LissRhod conjugates. The indirect protocol includes a 50 fold higher concentration of the amine group, and it allows the fluorophore a much longer time to crosslink (overnight as compared to 30 minutes).

The inventors found a resistance of double stranded regions to fragmentation, thereby making it difficult to obtain strong hybridization signals for probes complementary to certain hairpin regions of RNA and DNA. In these instances, urea was utilized to eliminate the influence of certain three-dimensional structures (such as hairpins) on the labeling-fragmentation procedure and to improve the signal for probes complementary to hairpin regions. The inventors found that the addition of urea to the invented protocol increases the sensitivity of the double stranded regions within the RNA molecule to fragmentation.

Surprisingly and unexpectedly, the inventors found that when other reagents are held constant, the addition of urea dramatically increased the sensitivity of RNA to hydrolysis with OP-Cu. For example, when 3.5 M–7.0 M urea was included in the reaction and the hydrogen concentration was lowered 10-fold to 10 mM, the same degree of RNA fragmentation and a higher hybridization signal was obtained, compared to when higher levels of hydrogen peroxide and no urea is utilized.

RNA/DNA Labeling with Fe-EDTA Detail

An Fe-EDTA radical generating system was employed for a sequence-nonspecific labeling method. The Fe-EDTA complex is negatively charged and thus does not interact directly with the DNA molecule. Instead, the Fe-EDTA complex, in the presence of hydrogen peroxide, produces hydroxyl radicals which have no charge and which therefore are able to diffuse into the DNA molecule. Hydroxyl radicals are able to abstract any of the hydrogen atoms from the carbon atoms within the deoxyribose residues of B-form DNA, but abstraction from the 4' and 5'-positions are the predominant pathways. Preference for individual hydrogen atoms was found to be H-5'>H-4'>H-2'=H-3'>H-1', which correlates with the accessibility of the individual hydrogen atoms to a solvent.

As with the OP-Cu method, a direct and an indirect labeling protocol were used to label DNA and RNA. Generally, exemplary Fe-EDTA protocols are found in M. A. Price et al. *Methods Enzymol*, 202, 194–219, Marshall, et al., *Biochemistry* 20, 244–250 and Tullius et al., *Methods Enzymol*. 155, 537–559, all incorporated herein by reference. Suitable results were obtained at 95° C. for 10 minutes.

The indirect Fe-EDTA protocol that gave the strongest hybridization signal was 1.5 mM Fe/10 mM $H_2O_2$/1 mM NaAsc (Table 4, treatment 6). The optimal indirect Fe-EDTA protocol required a 10 fold lower concentration of $H_2O_2$ than the direct protocol. PAGE gel electrophoresis data indicated that the optimal indirect Fe-EDTA protocol resulted in less fragmentation (FIG. 5A g) than the optimal direct Fe-EDTA protocol (FIG. 5A c). This result is consistent with the results for the Op-Cu system, in which the indirect protocol also required lower reactant concentrations and less fragmentation than the direct protocol. As was discussed above, this result may be due to differences in the fluorophores or differences in the direct and indirect protocols.

Fe-EDTA Direct Protocol

To maintain anaerobic conditions, all reagents are bubbled with a neutral fluid (such as argon, helium, or other relatively unreactive gases) before use, and the reaction solutions were bubbled with the fluid between each step. The Fe-EDTA complex consists of 0.5M EDTA and 0.25M ammonium iron (II) sulfate. The following concentrations are for illustrative purposes only inasmuch as commercial scales are considerably larger. Also, reaction times and temperatures may vary to take into consideration batch processing effects and the like.

In the laboratory scaled protocol, total reaction volume was 100 µl. RNA (10 or 20 µg), 20 µl 100 mM sodium phosphate (pH=7), DEPC treated $H_2O$, 7M urea, and the Fe-EDTA complex were combined and bubbled with argon. After bubbling, 1 µl of 100 mM LissRhod was added and solution was bubbled with argon and preheated for 3 minutes at 95° C. $H_2O_2$ and sodium ascorbate (NaAsc) were added. The reaction solution was again bubbled with argon and then heated to 95° C. for 10 to 30 min. Reaction was stopped by addition of 10 µl 1M thiourea and incubation in a room temperature water bath for 1 min. Reduction was carried out by addition of 10 µl of 200 mM sodium cyanoborohydride and incubation at room temperature in the dark for 30 min. Labeled RNA was precipitated in 96% ethanol/0.4M sodium acetate at −80° C. for at least 20 min. After centrifugation at 14,000 rpm for 5 minutes, RNA pellets were washed twice with ethanol. Excess LissRhod was removed by butanol treatment as described above. RNA pellets were suspended in 10 to 20 µl DEPC $H_2O$.

Indirect Labeling Protocol

As in the direct protocol above, the following concentrations are provide for illustrative purposes only. Commercial scale operations obviously require larger volumes and typical processing requirements.

In the laboratory protocol, for indirect labeling, LissRhod is replaced in the fragmentation protocol by 10 µl 0.5M ethylenediamine (EDA). After precipitation, the RNA pellet was dissolved in 60 µl or 100 µl 100 mM sodium carbonate (pH 9.0). The mixture was then transferred to an ampule containing Texas Red sulfonyl chloride (TexRed) (Molecular probes, Eugene, Oreg.), precooled with ice, and incubated on ice overnight. The reaction was stopped by adding 25 µl or 40 µl 1M acetic acid and the mixture was diluted with 200 µl 100 mM sodium acetate (pH 4). Excess TexRed was removed from RNA by butanol treatment as described above. RNA pellets were suspended in 10 to 20 µl DEPC $H_2O$.

Screening of several different reaction conditions demonstrated that the direct Fe-EDTA protocol that gave the highest hybridization signal was 1.5 mM Fe/10 mM $H_2O_2$/ 10 mM NaAsc (Table 1). PAGE Gel Electrophoresis demonstrated that this reaction condition produced RNA fragments between approximately 50 and 100b in length (FIG. 5A. c). Increasing the concentration of Fe to 15 mM resulted in an increase in the length of RNA (FIG. 5A, b) and a decrease in the hybridization signal (Table 4, treatment 1). As such, the inventors found that Fe inhibits fragmentation, which is resulting in a decrease in the hybridization signal. Increasing the level of $H_2O_2$ in addition to increasing the level of Fe resulted in almost complete degradation of the RNA (FIG. 5A, d) and a further decrease in the hybridization signal (Table 4, treatment 3).

Nucleic Acid Isolation and Preparation Detail

In one protocol, chip-attached probes specific for the Bacillus group of microorganisms were effectively hybridized with nucleic acids, which were labeled via the invented protocol.

RNA was isolated from frozen cell pellets of *Bacillus cereus* 9620, *Bacillus cereus* 3329, and *Bacillus thuringiensis* 4042B. *Bacillus thuringiensis* 4042B was used as a mimic of *Bacillus antracis,* as both have identical 16S rRNA sequences. Cells were lysed via standard bead beating protocol such as that disclosed in Sambrook et al., *Molecular Cloning, A Laboratory Manual,* $2^{nd}$ Ed. CSH (1989) and incorporated herein by reference. RNA was isolated by phenol extraction and precipitated by addition ammonium acetate and ethanol. Surprisingly and unexpectedly, the inventors found that this precipitation protocol allowed for the RNA to be stored at −80° C. overnight, without sustaining damage.

After centrifugation at 14,000 rpm for 5 minutes, RNA pellets were washed with ethanol, and suspended in water containing an RNAse inhibitor. One such exemplary inhibitor is DEPC (diethyl pyrocarbonate).

With regard to DNA preparation, 16S rDNA was synthesized by PCR amplification of bulk *B. cereus* 9620 and *B. anthracis* AMES DNA polymerase (available from Ambion, Austin, Tex.) using 11F and 1512 primers.

Two protocols, enumerated in the examples below have been developed. Both were successfully used for *B. medusa* labeling and fragmentation at the same time.

EXAMPLE 1

To assure anaerobic conditions, and just before the start of the reactions, all solutions are bubbled with argon. Ethylene diamine (EDA) is included in the initial reaction mixture in the presence of hydrogen peroxide and OP-Cu or EDTA-Fe. This initial step has a duration of approximately 30 minutes and occurs at approximately 45° C. The EDA reacts with the aldehyde groups of the DNA or RNA to form a Schiff base.

The labeling process is continued in the same reaction vessel by reducing the double bond in the base with a reducing agent such as sodium cyanoboro-hydride. This step has a duration of approximately 30 minutes and takes place at room temperature. The Schiff base is then reprecipitated with acetone. The product of this reduction is then labeled by adding Texas Red sulfonyl chloride (TexRed-SuCl) and subsequently hybridized with a microchip.

EXAMPLE 2

Anaerobic conditions are established as in Example 1, above. In this example, nucleic acids were modified with OP-Cu or EDTA-Fe in the presence of hydrogen peroxide and amino-dye Lissamine rhodamine B ethylenediamine (LissRH-EDA) over a period of approximately 30 minutes at 45° C.

The resulting LissRH-EDA-nucleic acid Schiff base was reduced with sodium cyanoborohydride in the same reaction vessel over a period of 30 minutes at room temperature. Alternatively, crosslinking of the dye and Schiff base reduction were integrated in one step.

The DNA microchips utilized in this study consisted of an array of polyacrylamide gel pads affixed to a glass slide. These gel pads served as three-dimensional supports for the immobilization of oligonucleotide probes. This DNA microchip technology requires random fragmentation and fluorescent labeling of target nucleic acids prior to hybridization. Nucleic acid fragmentation is necessary to reduce the size of the nucleic acid molecules so that they can easily enter the pore spaces of the polyacrylamide gel pads and access the oligonucleotide probes. Nucleic acid fragmentation also allows different regions of the target nucleic acid molecule to hybridize independently to each of the immobilized oligonucleotides.

Fluorescent labeling of target nucleic acids is required for hybridization detection. Although fluorescent labeling is less sensitive than radioactive labeling, fluorescent labeling offers several advantages. Fluorescent dyes do not pose radiation hazards, and thus their use and disposal is less problematic. In addition, fluorescent labels can be detected in real time with high resolution. Treatment of DNA or RNA with an oxidizing agent or free radical results in the production of a reactive abasic site on the nucleic acid molecule. This sort of modification protocol obtained after purine methylation is disclosed in Pruss, D. and Bavykin, S. G. (1997) *Methods,* 12, 36–47 and Pruss, D., Gavin, I. M., Melnik, S., and Bavkin, S. G. (1999) *Methods Enzymol.,* 304, 516–533, and incorporated herein by reference. Nucleic acid treatment with radical-generating coordination complexes is also disclosed in Gavin, I. M., Melnik, S. M., Yurina, N. P., Khabarova, M. I., and Bavykin, S. G. (1998) *Anal. Biochem.,* 263, 26–30 and incorporated herein by reference, for crosslinking of proteins to nucleic acids through the amino groups or through the imidazole rings of histidines. This reactive abasic site is useful for the direct crosslinking of nucleic acids to fluorophores containing amino groups, or for the indirect crosslinking of nucleic acids to amino reactive fluorophores through ethylenediamine (EDA). The inventors in the present invention utilize the radical generating systems to both fragment nucleic acids and in the same reaction produce reactive sites that would allow the crosslinking of the nucleic acid fragments to fluorophores.

RNA Isolation

Total RNA was isolated from frozen cell pellets of *Bacillus cereus* (str. 9620), and *Bacillus thuringiensis* (str. 4042B). Cells were lysed via standard bead beating protocol, as outlined supra. RNA was isolated by phenol extraction and precipitated by addition of 0.5 volumes of 7.5M ammonium acetate and 2.5 volumes of ethanol and storage at −80° C. overnight. After centrifugation at 14,000 rpm for 5 minutes, RNA pellets were washed with 80% ethanol, and suspended in DEPC (diethyl pyrocarbonate) treated H$_2$O.

DNA Preparation 16S rDNA was synthesized by PCR amplification of bulk DNA from *Bacillus cereus* 3329 with AmpliTaq DNA polymerase (Ambion, Austin, Tex.) using 11F and 1512R primers.

Comparison of Methods

To determine the effectiveness of the OP-Cu and Fe-EDTA systems, the hybridization signals obtained with these systems to the hybridization signal were compared with signals obtained with a Magnesium-Sodium Periodate labeling and fragmentation method developed by the inventors. Direct labeling and indirect labeling variations were ran using all three methods using *Bacillus cereus* 9620 bulk RNA. All three methods gave identical hybridization patterns and the hybridization signals for all three methods were approximately equivalent (FIG. 5 and Table 1).

In all three systems, indirect labeling produced 20 to 30% higher hybridization signals than direct labeling. This result is consistent with the results found for both the OP-Cu and Fe-EDTA methods.

An exemplary protocol of the invented comparison method follows herewith. It should be noted that the reaction volumes utilized are relative to all reactants. For the sake of illustration, specific reaction volumes are employed herein.

Given a total reaction volume of 100 μl, RNA (20 mg) and DEPC-treated H$_2$O were combined and preheated at 95° C. for 5 minutes. MgCl$_2$ was added to 60 mM and the reaction solution was heated at 95° C. for 40 minutes. Phosphatase treatment was carried out by addition of 3 μl 10× alkaline phosphatase buffer (Promega, Madison, Wis.) and 0.2 μl alkaline phosphatase (1μ/μl) (Promega, Madison, Wis.) and heating at 37° C. for 30 minutes. Oxidation was conducted by addition of 6.5 μl of 100 mM sodium periodate and incubation at room temperature for 20 minutes. Labeling was carried out by addition of 3.5 μl of 100 mM Lissamine rhodamine B ethylenediamine (LissRhod) (Molecular Probes, Eugene, Oreg.) and 1.65 μl of 1M HEPES (pH 7.5) and heating at 37° C. for 1 hour. Reduction was conducted by addition of 6.7 μl of 200 mM sodium cyanoborohydride and incubation at room temperature for 30 minutes. Labeled RNA was precipitated by addition of 15 volumes of 2% lithium perchlorate in acetone and stored at −20° C. for 20 min. After centrifugation at 14,000 rpm for 5 minutes, RNA pellets were washed twice with acetone and dried at 55° C. for 10 minutes.

Butanol Treatment

Excess LissRhod was removed from RNA by butanol treatment: RNA pellets were suspended in 300 μl DEPC treated H$_2$O, and samples were concentrated to 60 μl by removal of water with butanol. Treatment was repeated until butanol was free of color. RNA was precipitated in 15 volumes of 2% LiClO$_4$ in acetone at −20° C. for 20 min. After centrifugation at 14,000 rpm for 5 minutes, RNA pellets were washed twice with acetone, dried at 55° C. for 10 minutes, and suspended in 10 to 20 μl DEPC treated H$_2$O.

Fragmented and labeled RNA samples were analyzed by polyacrylamide gel electrophoresis.

Genus- and Species-specific Oligonucleotide Probes.

For selection of genus-specific probes, the 16S rRNA sequence from a specific microorganism belonging to the genus was used to create a set of all possible 20b oligonucleotide probes (the set consisted of L-19 oligonucleotides, where L denotes the length of the entire 16S rRNA sequence). Each potential probe was tested against all available 16S rRNA sequences (GenBank and RDP) by a function that estimates the relative duplex stability according to the number and position of mismatches. If the 16S rRNA of any microorganism that did not belong to the genus of interest formed stable duplexes with any oligonucleotide considered as a probe for the microchip, this oligonucleotide was excluded from the list of probes. A similar procedure was carried out for the selection of species-specific probes. A final set of 15 oligonucleotide probes each approximately 20b in length (Table 2) was selected for application to the DNA microchip.

The selected oligonucleotides (Table 2) were synthesized on an automatic DNA/RNA synthesizer (Applied Biosystems 394) using standard phosphoramide chemistry. A 5'-Amino-Modifier C$_6$ (Glen Research, Sterling, Va.) was linked to the 5'-end of the oligonucleotides.

TABLE 2

Oligonucleotide probes on DNA microchip

| Probe | Length | Sequence | 16S rRNA 5'-end location | Target |
|---|---|---|---|---|
| 1 | 17 | (SEQ. ID. NO. 1) | 1400 | Universal |
| 2 | 18 | (SEQ. ID. NO. 2) | 529 | Universal |
| 3 | 18 | (SEQ. ID. NO. 3) | 345 | Eubacteria |
| 4 | 17 | (SEQ. ID. NO. 4) | 938 | Eubacteria |
| 5 | 20 | (SEQ. ID. NO. 5) | 203 | *B. cereus* Group |
| 6 | 20 | (SEQ. ID. NO. 6) | 455 | *B. cereus* Group |
| 7 | 20 | (SEQ. ID. NO. 7) | 1038 | *B. cereus* Group |
| 8 | 20 | (SEQ. ID. NO. 8) | 1257 | *B. cereus* Group |
| 9 | 23 | (SEQ. ID. NO. 9) | 175 | *B. cereus* strs. 9620 and *B. thuringiensis* str. 4042B |
| 10 | 20 | (SEQ. ID. NO. 10) | 186 | *B. cereus* strs. 9620 and *B. thuringiensis* str. 4042B |
| 11 | 20 | (SEQ. ID. NO. 11) | 186 | *B. mycoides* str. 6462 m |
| 12 | 23 | (SEQ. ID. NO. 12) | 187 | *B. mycoides* str. |

A microchip consisting of an array of 100×100×20 μm polyacrylamide gel pads affixed to a glass slide and spaced 100 μm from each other was manufactured via photopolymerization as disclosed in Gushin et al. *Anal Biochem* 250, 203–211 (1997) and incorporated herein by reference. The gel pads were activated as described in Proudnikov et al. *Nucl. Acids Res* 24, 4535–4542, incorporated herein by reference. This resulted in the production of aldehyde groups within the gel pads. Each oligonucleotide was applied to a unique gel pad within the array and each gel pad received a preselected volume (for example 6 nL) of the oligonucleotide solution. The hybridization solutions and protocol are disclosed in the references cited above. Generally, though, the hybridization solution consisted of DEPC treated H$_2$O, 3M GuSCN, 0.5M EDTA (pH 7.0), 1M HEPES (pH 7.5), and RNA solution. The hybridization solution was filtered, and then heated at 95° C. for 3 min before placed on ice. The hybridization solution was added to a hybridization chamber, and the hybridization chamber was affixed to a microchip. The microchip was allowed to hybridize overnight at room temperature in the dark. After hybridization, the chamber and hybridization solution were removed from the microchip, and the microchip was washed with NaCl, sodium phosphate at neutral pH, EDTA, and Tween. After washing the microchip was imaged using a fluorescence microscope, and CCD camera.

Analysis of Hybridization Data

The fluorescent intensity of each gel element was quantified from the WinView image using LabView software. The score for each gel element was calculated by subtracting the averaged fluorescent intensity of the area immediately surrounding the gel element (i.e. the background) from the averaged fluorescent intensity of the entire area of the gel element. To compare experimental treatments, the hybridization signal for each experimental treatment was calculated by averaging the scores for the four oligonucleotide probes targeting the anthracis group, probes 5 to 8 (Table 2). The intensity of the hybridization signal was used to assess the effectiveness of different reaction parameters for the fragmentation and labeling procedures. Hybridization Tables 3–6 represent average signals calculated from data obtained in a single experiment. Within each experiment, treatments were replicated from 2 to 4 times, and the variation in hybridization signals for each treatment was less than 20%.

TABLE 3

Indirect fluorescent RNA labeling with OP-Cu*

| Treatment | Nucleic Acid | Concentrations (mM) | | | | Texas Red | Hybridization*** Signal (u/μg/sec) |
|---|---|---|---|---|---|---|---|
| | | OP | Cu | $H_2O_2$ | EDA | | |
| 1 | RNA** | 15.0 | 1.50 | 100 | 50 | 20.0 | 50 |
| 2 | RNA** | 1.5 | 0.15 | 100 | 50 | 20.0 | 930 |
| 3 | RNA** | 1.5 | 0.15 | 10 | 50 | 20.0 | 1700 |

*All fragmentation and labeling reactions were run for 30 min. at 45° C.
**B. thuringiensis 4042B bulk RNA
***Average of hybridization signal from probes 5, 6, 7, 8.

TABLE 4

Direct method of fluorescent RNA labeling with Fe-EDTA*

| Treatment | Nucleic Acid | Concentrations (mM) | | | | Hybridization*** Signal (u/μg/sec) |
|---|---|---|---|---|---|---|
| | | Fe | $H_2O_2$ | NaAsc | Liss. rhod. | |
| 1 | RNA** | 15.0 | 10 | 1 | 1 | 55 |
| 2 | RNA** | 1.5 | 10 | 1 | 1 | 280 |
| 3 | RNA** | 150.0 | 100 | 1 | 1 | 14 |
| 4 | RNA** | 15.0 | 10 | 10 | 1 | 52 |

*All fragmentation and labeling reactions were run for 10 min. at 95° C.
**B. cereus 9620 bulk RNA
***Average of hybridization signal from probes 5, 6, 7, 8.

TABLE 5

Direct OP-Cu RNA* labeling: variation in reaction parameters

| Treatment | Temp (° C.) | Time (min.) | Concentrations (mM) | | | Hybridization*** Signal (u/μg/sec) |
|---|---|---|---|---|---|---|
| | | | OP | Cu | $H_2O_2$ | |
| 1 | 45 | 30 | 15.0 | 1.50 | 100 | 650 |
| 2 | 70 | 30 | 15.0 | 1.50 | 50 | 200 |
| 3 | 70 | 30 | 1.50 | 0.15 | 10 | 475 |
| 4 | 95 | 30 | 1.50 | 0.15 | 10 | 1100 |
| 5 | 95 | 10 | 1.50 | 0.15 | 10 | 710 |
| 6 | 95 | 10 | 15.0 | 1.50 | 50 | 150 |
| 7 | 95 | 10 | 15.0 | 1.50 | 10 | 1150 |
| 8 | 95 | 10 | 1.5 | 0.15 | 50 | 500 |
| 9 | 95 | 10 | 1.5 | 0.15 | 10 | 760 |

*B. cereus 9620 bulk RNA
**Average of hybridization signal from probes 5, 6, 7, 8.

TABLE 6

Direct OP-Cu RNA* labeling** with variations in urea concentration

| Treatment | Urea (M) | Concentrations (mM) | | | Hybridization*** Signal (u/μg/sec) |
|---|---|---|---|---|---|
| | | OP | Cu | $H_2O_2$ | |
| 1 | 0.0 | 15.0 | 1.5 | 100 | 570 |
| 2 | 3.5 | 15.0 | 1.5 | 100 | 90 |
| 3 | 3.5 | 15.0 | 1.5 | 10 | 815 |
| 4 | 7.0 | 15.0 | 1.5 | 100 | 56 |
| 5 | 7.0 | 15.0 | 1.5 | 10 | 280 |

*B. cereus 9620 bulk RNA
**All fragmentation and labeling reactions were run for 30 min. at 45° C.
***Average of hybridization signal from probes 5, 6, 7, 8.

Another DNA intermediate that may be used for labeling with aminoderivatives of fluorescent dyes is metastable lactone. (Molecule number 4 in FIG. 1B) This lactone is an intermediate in both aerobic and anaerobic H-1' abstraction pathways. Reaction of this lactone with a primary amine leads to products depicted as Molecules 5 and 6 in FIG. 1.

Denaturing Agent Detail

Optionally, denaturing agents are included in the reactions to disrupt the secondary structure of the 16S rRNA molecule. This facilitates easier fragmentation by the hydroxyl radicals. The inventors found that with the other reagents held constant and the reaction run at 45° C. for 30 min., the addition of denaturants (such as formamide, guanidine chloride, ethyl carbonate, urethane, carbonic acid, and urea) dramatically increased the sensitivity of RNA to hydrolysis with OP-Cu.

For example, when the denaturant urea is utilized, fragmentation increases substantially, as shown by the increase in fragmentation (FIG. 4B, b, c, e) and the decrease in hybridization signal (Table 6, treatments 1, 2 and 4). Specifically, when 3.5M urea is included in the reaction and the hydrogen peroxide concentration is lowered 10-fold to 10 mM, the same degree of RNA fragmentation is obtained (FIG. 4B, d) as well as a higher hybridization signal (Table 6, treatment 3), compared with the treatment without urea (FIG. 4B, b and Table 6 treatment 1). For the OP-Cu reaction run at 45° C. for 30 min., 3.5M urea with 10 mM $H_2O_2$ gave the highest hybridization signal (Table 6, treatment 3). When the OP-Cu reaction is run at 45° C., the optimal condition is a 3.5M concentration of urea.

Figure 7:
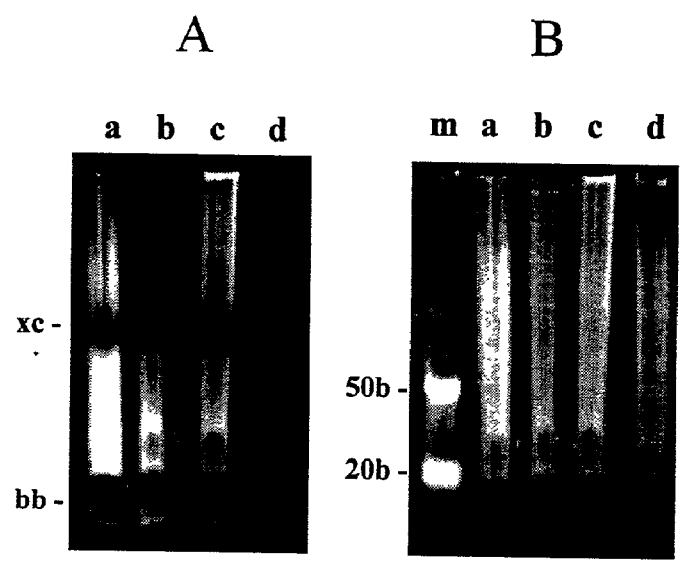
FIGS. 7A–B illustrate ethidium bromide stained gel images, in accordance with features of the present invention.

When the OP-Cu reaction (FIG. 7) was run at 95° C., urea is not necessary. FIG. 7A is a fluorescence image while FIG. 7B is a ethidium bromide stain gel image for the OP-Cu and Fe-EDTA reactions. Lanes a and c show the reaction occurring in the absence of urea and lanes b and d depict the reaction with 3.5 M urea present. For the Fe-EDTA protocol run at 95° C. for 10 min., urea resulted in an inhibition of fragmentation (FIG. 7d). Therefore for the Fe-EDTA reaction run at 95° C. urea was not necessary.

Reduction Step

An experiment was run for both the OP-Cu and the Fe-EDTA protocols in which the reductant, $NaCNBH_3$, was included in the reaction with all of the other reagents. For the OP-Cu protocol, the inclusion of the reductant in the reaction step produced a higher level of fragmentation (FIG. 6A, b) to the standard protocol (FIG. 6A, a) as well as a 1.5 fold increase in hybridization signal. This change in the standard OP-Cu protocol reduced the time required for the protocol by 30 minutes.

For the Fe-EDTA protocol, the inclusion of NaCNBH$_3$ in the reaction step produced an equivalent level (FIG. 6A, d) of fragmentation to the standard protocol (FIG. 6A, c). Also, the inclusion of the reductant resulted in a decrease in the hybridization signal 3-4 fold. At the same time, complete exclusion of the reduction step from the Fe-EDTA protocol resulted in no changes in labeling (FIG. 6B) or in fragmentation (FIG. 6C) of RNA.

While the invention has been described with reference to details of the illustrated embodiment, these details are not intended to limit the scope of the invention as defined in the appended claims.

The embodiment of the invention in which an exclusive property or privilege is claimed is defined as follows:

1. A method for labeling DNA molecules, the method comprising:
    a) contacting DNA molecules with hydrogen peroxide and 1,10-phenanthroline-Cu(II) for a time and at a concentrations sufficient to produce DNA single strand scission and free-aldehyde moieties on either the 5' or 3' end of molecules at the site of scission;
    b) reacting the aldehyde moieties with amine to produce a condensation product; and
    c) labeling the condensation product by crosslinking with a lable such that 90 percent of the crosslinking occurs at the 5'-end or the 3'-end of the DNA molecules.

2. The method as recited in claim 1 wherein the step of labeling the condensation product further comprises:
    a) reducing the condensation product; and
    b) contacting the reduced condensation product with a chromophore.

3. The method as recited in claim 1 wherein the amine is a primary amine.

4. The method as recited in claim 1 wherein the amine is ethylene diamine or hydrazine or aminated biotin.

5. The method as recited in claim 1 wherein the contacting step occurs in an anaerobic environment.

6. The method as recited in claim 1 wherein the step of labeling the condensation product further comprises reducing the condensation product and cross-linking the reduced condensation product with a label in one reaction step.

7. The method as recited in claim 1, wherein the step of contacting the DNA molecules with 1,10-phenanthroline-Cu (II) includes contacting the nucleic acid with denaturing agent.

8. A method for labeling DNA molecules, the method comprising:
   a) producing free radicals by reacting hydrogen peroxide with 1,10-phenanthroline-Cu (II);
   b) contacting the produced free radicals with DNA molecules to produce single stranded scission-free nucleic acid bases and aldehyde forms of deoxyribose at either the 5' ends or 3' ends at the site of scission;
   c) contacting the aldehyde forms with an amine to produce a condensation product;
   d) reducing the condensation product; and
   e) labeling the reduced condensation product by crosslinking with a label, such that 90 percent of the crosslinking occurs at the 5'-end or the 3'-end of the DNA molecules.

9. The method recited in claim 8 wherein steps d and e occur simultaneously.

10. The method recited in claim 8 wherein step e occurs in anaerobic conditions.

11. The method as recited in claim 8 wherein the DNA is double stranded and wherein the step of contacting the free radicals with the nucleic acids is preceded by the addition of a double-strand weakening agent.

12. The method as recited in claim 11 wherein the double-strand weakening agent is a denaturing agent selected from the group consisting of carbonic acid, urea, ethyl carbonate, cyanamide, urethane, and combinations thereof.

13. The method as recited in claim 8 wherein the DNA is modified at temperatures below the boiling point of water.

14. The method as recited in claim 9 wherein the crosslinking occurs at between 0° C. and 95° C.

15. The method as recited in claim 8 wherein the free radicals are contacted with the DNA in an anaerobic atmosphere.

* * * * *

UNITED STATES PATENT AND TRADEMARK OFFICE
CERTIFICATE OF CORRECTION

PATENT NO. : 7,208,269 B2
APPLICATION NO. : 10/057753
DATED : April 24, 2007
INVENTOR(S) : Bavykin et al.

Page 1 of 1

It is certified that error appears in the above-identified patent and that said Letters Patent is hereby corrected as shown below:

At Column 24, Line 58 Claim 1: replace the word "lable" with --label--, so as to read --a label such--.

At Column 25, Line 11 Claim 7: insert the word --a-- between the words "with" and "denaturing", so as to read --with a denaturing--.

Signed and Sealed this

Nineteenth Day of February, 2008

JON W. DUDAS
*Director of the United States Patent and Trademark Office*

```
                       SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
        (A) LENGTH: 17 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 1:

ACG GGC GGT GTG TRC AA                                             17

(2) INFORMATION FOR SEQ ID NO: 2:

(i) SEQUENCE CHARACTERISTICS:
        (A) LENGTH: 18 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 2:

GWA TTA CCG CGG CKG CTG                                            18

(2) INFORMATION FOR SEQ ID NO: 3:

(i) SEQUENCE CHARACTERISTICS:
        (A) LENGTH: 18 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 3:

TGC CTC CCG TAG GAG TCT                                            18

(2) INFORMATION FOR SEQ ID NO: 4:

(i) SEQUENCE CHARACTERISTICS:
        (A) LENGTH: 17 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes
```

-continued

```
        (xi) SEQUENCE DESCRIPTION: SEQ ID NO: 4:

ACC GCT TGT GCG GGC CC                                              17

(2) INFORMATION FOR SEQ ID NO: 5:

(i) SEQUENCE CHARACTERISTICS:
          (A) LENGTH: 20 bases
          (B) TYPE: nucleic acid
          (C) STRANDEDNESS: Not Applicable
          (D) TOPOLOGY: linear (ii) MOLECULE TYPE: Genomic DNA (iii) HYPOTHETICAL: yes (xi) SEQUENCE DESCRIPTION: SEQ ID NO: 5:

CGA AGC CGC CTT TCA ATT TC                                          20

(2) INFORMATION FOR SEQ ID NO: 6:

(i) SEQUENCE CHARACTERISTICS:
          (A) LENGTH: 20 bases
          (B) TYPE: nucleic acid
          (C) STRANDEDNESS: Not Applicable
          (D) TOPOLOGY: linear (ii) MOLECULE TYPE: Genomic DNA (iii) HYPOTHETICAL: yes (xi) SEQUENCE DESCRIPTION: SEQ ID NO: 6:

CAA CTA GCA CTT GTT CTT CC                                          20

(2) INFORMATION FOR SEQ ID NO: 7:

(i) SEQUENCE CHARACTERISTICS:
          (A) LENGTH: 20 bases
          (B) TYPE: nucleic acid
          (C) STRANDEDNESS: Not Applicable
          (D) TOPOLOGY: linear (ii) MOLECULE TYPE: Genomic DNA (iii) HYPOTHETICAL: yes (xi) SEQUENCE DESCRIPTION: SEQ ID NO: 7:

TGT CAC TCT GCT CCC GAA GG                                          20

(2) INFORMATION FOR SEQ ID NO: 8

(i) SEQUENCE CHARACTERISTICS:
          (A) LENGTH: 20 bases
          (B) TYPE: nucleic acid
          (C) STRANDEDNESS: Not Applicable
          (D) TOPOLOGY: linear (ii) MOLECULE TYPE: Genomic DNA (iii) HYPOTHETICAL: yes (xi) SEQUENCE DESCRIPTION: SEQ ID NO: 8:

CGG TCT TGC AGC TCT TTG TA                                          20

(2) INFORMATION FOR SEQ ID NO: 9:

(i) SEQUENCE CHARACTERISTICS:
          (A) LENGTH: 23 bases
          (B) TYPE: nucleic acid
```

```
            (C) STRANDEDNESS: Not Applicable
            (D) TOPOLOGY: linear (ii) MOLECULE TYPE: Genomic DNA (iii) HYPOTHETICAL: yes (xi) SEQUENCE DESCRIPTION: SEQ ID NO: 9:

ATG CGG TTC AAA ATG TTA TCC GG                                              23

(2) INFORMATION FOR SEQ ID NO: 10:

(i) SEQUENCE CHARACTERISTICS:
            (A) LENGTH: 20 bases
            (B) TYPE: nucleic acid
            (C) STRANDEDNESS: Not Applicable
            (D) TOPOLOGY: linear (ii) MOLECULE TYPE: Genomic DNA (iii) HYPOTHETICAL: yes (xi) SEQUENCE DESCRIPTION: SEQ ID NO: 10:

TTC GAA CCA TGC GGT TCA AA                                                  20

(2) INFORMATION FOR SEQ ID NO: 11:

(i) SEQUENCE CHARACTERISTICS:
            (A) LENGTH: 20 bases
            (B) TYPE: nucleic acid
            (C) STRANDEDNESS: Not Applicable
            (D) TOPOLOGY: linear (ii) MOLECULE TYPE: Genomic DNA (iii) HYPOTHETICAL: yes (xi) SEQUENCE DESCRIPTION: SEQ ID NO: 11:

TTC GAA CTA TGC AGT TCA AA                                                  20

(2) INFORMATION FOR SEQ ID NO: 12:

(i) SEQUENCE CHARACTERISTICS:
            (A) LENGTH: 23 bases
            (B) TYPE: nucleic acid
            (C) STRANDEDNESS: Not Applicable
            (D) TOPOLOGY: linear (ii) MOLECULE TYPE: Genomic DNA (iii) HYPOTHETICAL: yes (xi) SEQUENCE DESCRIPTION: SEQ ID NO: 12:

CAA TTT CGA ACT ATG CAG TTC AA                                              23
```